United States Patent [19]

Mikuma et al.

[11] Patent Number: 4,990,630
[45] Date of Patent: Feb. 5, 1991

[54] 2,3-DIAMINOACRYLONITRILE DERIVATIVES AND PROCESS FOR MAKING THE SAME

[75] Inventors: Katsunori Mikuma; Nobuhiro Umeda, both of Kurashiki; Tomio Yagihara; Isami Hamamoto, both of Odawara, all of Japan

[73] Assignee: Nippon Soda Co., Ltd., Tokyo, Japan

[21] Appl. No.: 398,969

[22] Filed: Aug. 28, 1989

Related U.S. Application Data

[63] Continuation-in-part of Ser. No. 189,245, Apr. 11, 1988, abandoned.

[30] Foreign Application Priority Data

Aug. 13, 1986 [JP] Japan ............................ 61-189807
Sep. 1, 1986 [JP] Japan ............................ 61-205581
Jul. 8, 1987 [JP] Japan ............................ 62-170638

[51] Int. Cl.$^5$ ............... C07D 307/64; C07D 307/91; C07C 253/10; C07C 255/08
[52] U.S. Cl. .................................. 549/460; 558/332; 558/335; 558/347; 558/348; 558/379; 549/460; 549/461; 549/496; 549/491; 549/479; 549/65
[58] Field of Search ............. 558/332, 335, 347, 348, 558/379; 549/479, 491, 496, 65, 466, 460, 461

[56] References Cited

U.S. PATENT DOCUMENTS

4,734,499 3/1988 Hickmann .................. 558/332

Primary Examiner—Mary C. Lee
Assistant Examiner—J. Richter
Attorney, Agent, or Firm—George B. Oujevolk

[57] ABSTRACT

The present invention relates to a 2,3-diaminoacrylonitrile derivative or salts thereof, having the formula

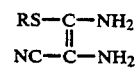

wherein R represents an alkyl group (which may be substituted by unsubstituted or substituted phenyl groups, halogen atoms, $C_{1-6}$ alkoxycarbonyl groups, carboxy groups, $C_{1-6}$ alkoxycarbonyl $C_{1-6}$ alkylthio groups, hydroxy groups, mercapto groups, cycloalkyl groups or heterocyclic groups containing oxygen atoms); an alkenyl group; a cycloalkyl group; an aryl group (which may be substituted by halogen atoms, $C_{1-6}$ alkyl groups, nitro-groups, unsubstituted or substituted phenyl or phenoxy groups or heterocyclic groups containing oxygen atoms or sulfur atoms).

The 2,3-diaminoacrylonitrile derivative can be used as starting materials for the production of pharmaceutical and/or agricultural intermediates such as cyanoimidazoles, cyanopyrazines or other cyano-substituted heterocycles.

5 Claims, No Drawings

2,3-DIAMINOACRYLONITRILE DERIVATIVES AND PROCESS FOR MAKING THE SAME

This application is a continuation-in-part of U.S. Patent application Ser. No. 189,245, filed 4/11/88, now abandoned.

TECHNICAL FIELD

The present invention relates to new 2,3-diaminoacrylonitrile derivatives where the 3-position of 2,3-diaminoacrylonitrile is substituted by alkylthio, aralkylthio, alkenylthio, cycloalkylthio and arylthio groups.

The 2,3-diaminoacrylonitrile derivatives of this invention can be used as starting materials for the manufacture of pharmaceutical and/or agricultural intermediates such as cyanoimidazoles, cyanopyrazines and cyano-substituted heterocycles.

They can also be used as materials for the manufacture of diaminomaleonitrile, known as a pharmaceutical intermediate.

BACKGROUND ART

Some of the compounds derived from hydrogen cyanide are known as useful starting materials for the manufacture of pharmaceutical and/or agricultural intermediates. For example, cyanogen $(CN)_2$, a dimer of hydrogen cyanide, 2minomalononitrile $H_2NCH(CN)_2$, a posturated trimer, tetramer such as diaminomaleonitrile $H_2N(CN)C=C(CN)NH_2$ and diiminosuccinonitrile.

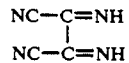

Of these compounds, 2-aminomalononitrile is too unstable to be isolated from polymerization of hydrogen cyanide. Generally it is prepared by other tedius method and exists as p-toluenesulfonate, which also is so unstable that it undergoes decomposition and discoloration. Moreover, it is too expensive to be used as industrial materials.

It is well know that hydrogen cyanide polymerizes easily in the presence of catalytic amount of a base to give undesired polymers unless the reaction conditions are well controlled, Usually, by controlling reaction conditions, hydrogen cyanide can be tetramized to give diaminomaleonitrile.

Actually, we have already disclosed in the United Kingdom Patent specication No. 1472439 that an efficient process for the production of diaminomaleonitrile which comprises tetramerizing hydrogen cyanide in liquid phase in the presence of a base catalyst such as triethylamine and a cocatalyst such as diphenyl disulfide at a temperature of 45°–7020 C. This fact suggests that a basic catalyst may be the polymerization initiator and a disulfide may be the polymerization regulator.

An object of the invention is to provide 2,3-diaminoacrylonitrile derivatives, a new and stable trimer of hydrogen cyanide, which similar to 2-aminomalononitrile, can be used as starting materials for the preparation of a wide variety of organic compounds.

A further of the present invention is to provide the method of producing these derivatives at a moderate price.

DISCLOSURE OF INVENTION

In the course of the mechanistic studies on the formation of diaminomaleonitrile by tetramerization of hydrogen cyanide the inventors discovered stable derivatives of 2,3-diaminoacrylonitrile, a new type of trimer of hydrogen cyanide, and thus have completed this invention. The present invention relates to the 2,3-diaminoacrylonitrile derivatives, or their salts, having the formula (I):

wherein R represent an $C_{1-18}$ alkyl group (which may be substituted by unsubstituted or substituted phenyl groups, halogen atoms, $C_{1-14}$ alkoxycarbonyl groups, carboxy groups, $C_{1-2}$ alkoxycarbonyl $C_{1-2}$ alkylthio groups, hydroxy groups, mercapto groups or heterocyclic groups containing oxygen and sulfur atoms); an $C_{3-15}$ alkenyl group; a $C_{5-6}$ cycloalkyl group; a naphthyl group; a benzofuranyl group; or a phenyl group (which may be substituted by halogen atoms, $C_{1-4}$ alkyl groups, cycloalkyl groups, nitro groups, unsubstituted or substituted phenyl or phenoxy groups).

The 2,3-diaminoacrylonitrile derivatives expressed by the formula (I) above can normally be isolated as crystals in the form of p-toluenesulfonates, hydrochlorides or other salts. These salts are quite stable and can be purified by recrystalization or other normal methods.

Further, free of these salts are comparatively stable in aprotic solvents and highly reactive polyfunctional compounds.

BEST MODE FOR CARRYING OUT THE INVENTION

The 2,3-diaminoacrylonitrile derivatives having the formula (I) can be manufactured by the following methods.

(1) Method were hydrogen cyanide is used (hereunder called manufacturing method 'a')

This method provides a process for the preparation of 2,3-diaminoacrylonitrile derivatives which comprise reacting hydrogen cyanide with a disulfide in the presence of a base.

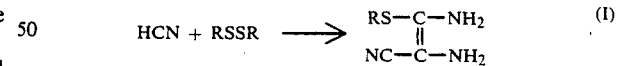

Normally the reaction is carried out at room temperature and under atmospheric pressure, though the levels of the temperature and pressure vary with the type of solvents used and the amount of their use.

The reaction is carried out in the presence of a disulfide and a base at a temperature of 0°–40° C., preferably 5 to 20° C. The reaction may take place at a temperature below 0° C., but a longer reaction time is required. When the reaction temperature is above 40° C., it is apt to cause overpolymerization, and the formation of diaminomaleonitrile become predominent. In order to. separate the desired product, alkali is added to the reaction mixture to exclude an excess amount of hydrogen cyanide, and to the resulting organic layer is then added an organic acid such as oxalic acid, sulfonic acids such as p-toluenesulfonic acid and naphthalenesulfonic acid, or inorganic acids such as hydrochloric acid and phosphoric acid to thereby isolate relevant acid salts of 2,3-diaminoacrylonitrile derivatives.

Usually, for further reaction these salts obtained it is enough to use by filtration followed by rinsing with such solvents as n-hexane, diethylether and acetonitrile. Recrystalization form acetonitrile may be recommendable for further purification.

The salts of 2,3-diaminoacrylonitrile derivatives isolated from reaction mixture are treated by alkali to give readily intended products in free forms.

The organic disulfides usable are aliphatic, aromatic compounds containing the bond —S—S—, for example, dialkyl disulfide wherein alkyl is, for example, alkyl containing 1 to 18, preferably 1 or 2, carbon atoms, diaryl disulfide having at least one halogen tom, methyl, nitro or ethyl substituent, preferably being, for example, diphenyl disulfide, di-p-chlorophenyldisulfide and di-p-methylphenyl disulfide.

When unsymmetical disulfide are used, two kinds of 2,3-diaminoacrylonitrile having a different RS group at 3-position may be obtained.

The organic solvents may be provided by a wide variety of organic liquids. The principal requirement for such solvent are that they are liquid under the condition employed and inert to the reactant and product. The employable solvents are, for example, alcohols such as ethanol, polar aprotic solvents such as acetonitrile, dimethylformamide and non-polar aprotic solvents such as benzene and xylene.

Their combined use are also possible.

The basic catalysts usable are alkali metal cyanides, such as sodium cyanide and potassium cyanide, alkali metal carbonates such as sodium carbonate and potassium carbonate, ammonia, and alkylamines having 1 to 4 carbon atoms in the or each alkyl group which include dialkyl and trialkylamines such as trietylamine and tributylamine, pyridine and diazabicycloundecene. The amount of the organic solvent, when used, is not critical. A range of molar concentration (mol/l) of each component for carring out this process are generally 0.5–2.5 for the disulfide, 0.3–10.5 for base and 0.5–53 for hydrogen cyanide.

Molar ratio of disulfide : base: hydrogen cyanide is at least 1:1:1, preferably 1:2:6.

Extraction from alkali can be carried out using any organic solvent which possesses limited solubility in water in the presence of salts. Suitable solvents are esters such as ethyl acetate, hydrocarbons such as benzene toluene, xylene and haloalkanes such chloroform.

Purification can be done by recrystallization from any solvent, for example, aromatic hydrocarbons, alcohols and haloalkanes.

(2) Method where 2-aminomalononitrile is used (hereunder called the manufacturing method 'b'):

$$H_2N-C(CN)_2H + RSSR, RSH\ or\ RSCCH_3 \xrightarrow{\quad}$$
$$\qquad\qquad\qquad\qquad\qquad\qquad\overset{O}{\underset{\|}{}}$$

(VI)  (II)  (III)  (IV)

$$\begin{array}{c}RS-C-NH_2\\ \|\\ NC-C-NH_2\end{array}$$

(I)

Reactions are allowed to proceed in an organic solvent in the presence of a base. For the organic solvent and the base, the items specified for the manufacturing method 'a' can be used and so can alcohols.

2-aminomalononitrile as expressed by the formula (VI) is so unstable that normally salts of P-toluenesulfonic acid, etc. are used.

After the reactions are completed, the similar procedures operated under the manufacturing method 'a' are carried out to obtain salts or free forms of intented products.

(3) Manufacturing method:

In the 2,3-diaminoacrylonitrile derivatives having the formula (I), depending on the type of the substituent expressed by R, exchange reactions of (I) with R'SH (VII) shown by the following scheme, can also produce the compounds (VIII) which the invention concerns.

$$\begin{array}{c}RS-C-NH_2\\ \|\\ NC-C-NH_2\end{array} + R'SH \longrightarrow \begin{array}{c}R'S-C-NH_2\\ \|\\ NC-C-NH_2\end{array} + RSH$$

(I)  (VII)  (VIII)  (IV)

The structure of the compound of the invention has been determined from the result of IR, NMR, MASS or other analyses.

The present invention is described in more detail by using examples. The scope of the invention, however, is by no means limited by these examples.

EXAMPLE 1

(Compound No. 1)

$$HCN + Ph-SS-Ph \xrightarrow[\text{2 p-toluenesulfonic acid}]{\text{1 Triethylamine}}$$

$$\begin{array}{c}Ph-S-C-NH_2\\ \|\\ NC-C-NH_2\end{array} \cdot HO_3S-\langle\rangle-CH_3$$

A solution of diphenyl disulfide (1 g), triethylamine (3 g) and hydrogen cyanide (7 g) in aceonitrile (21 g) was stirred for 1 hour at room temperature. To the residue left after evaporation of the solvent, p-toluenesulfonic acid (1.5 g) was added with well stirring to give a light-yellow precipitate (2.3 g) which was collected by filtration, washed thoroughly with n-hexane and dried in vacuo. Recrystallization form acetonitrile gave white crystales: m.p. 148°–149° C. (dec.)

Anal. Calcd for $C_{16}H_{17}N_3O_3S_2$; C, 52.9; H, 4.7; N, 11.6; S, 17.6; Found: C, 52.9; H, 4.4; N, 11.6; S, 17.5.

This compound was identified as 2,3-diamino-3-(phenylthio)acrylonitrile p-toluenesulfonate (Compound No. 1) by its I.R. and N.M.R. spectra.

EXAMPLE 2

(Compound No. 1)

$$HCN + Ph-SS-Ph \xrightarrow[\text{2 p-toluenesulfonic acid}]{\text{1 Triethylamine}}$$

-continued

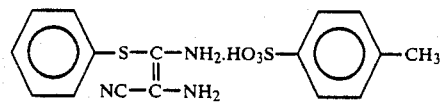

A solution of diphenyl disulfide (8 g), triethylamine (10 g) and hydorgen cyanide (18 g) in xylene (60 ml) was stirred for 50 minutes at room temperature. The tar left after evaporation of the solvent under reduced pressure was filtered, and a solution of p-toluenesulfonic acid (20 g) in acetonitrile (50 ml) was added to the filtrate. A light yellow precipitate formed was collected by filtration, thoroughly washed successively with acetonitrile and n-hexane, dried in vacuo, and recrystalized from acetonitrile to give light-yellow crystals (5.7 g): m.p.148°-149° C. (dec.) The infrared spectrum of this compound was identical with that of 2,3-diamino-3-(phenylthio)acrylonitrile p-toluenesulfonate obtained in example 1.

EXAMPLE 3

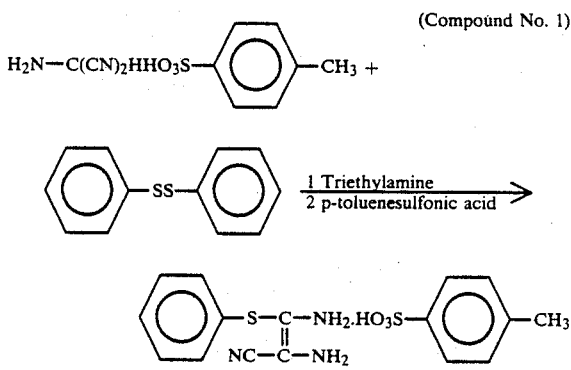

To a solution of triethylamine (2 g) and diphenyl disulfide (2 g) in acetonitrile (30 ml) was added 2-aminomalononitrile p-toluenesulfonate (1 g) with stirring for 10 minutes at room temperature. After removal of a half volume of the solvent, p-toluenesulfonic acid (2 g) was added to the residue. Work-up in an analogous manner as described in example 1 gave white crystals: m.p. 148°-149° C. (dec.)

The infrared spectrum of this compound was identical with that of 2,3-diamino-3-(phenylthio)acrylnotrile p-toluenesulfonate obtained in example 1.

EXAMPLE 4

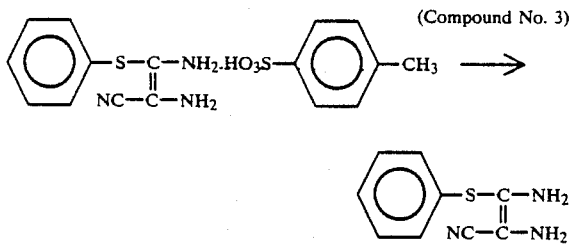

A suspension of 2,3-diamino-3-(phenylthio)acrylonitrile p-toluenesulfonate (10 g) obtained in example 1 in ethyl acetate (100 ml) was treated with saturated sodium carbonate solution (80 ml) at room temperature. The organic layer was separated, washed with brine and dried over magnesium sulfate. Removal of the solvent under reduced pressure left yellow crystales which were recrystallized from chloroform-n-hexane as light yellow needles: m.p. 86.5°-87.5° C. (dec.)

This compound was identified as 2,3-diamino-(3-phenylthio)acrylonitrile (Compound No. 3) by its I.R., N.M.R., and MASS spectra.

EXAMPLE 5

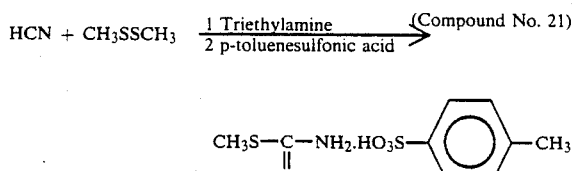

To a chilled solution of dimethyl disulfide (18.8 g) and triethylamine (40 g) in benzene (250 ml) was added hydrogen cyanide (48 ml) and stirred for 1.5 hours at room temperature. The reaction mixture was poured into an ice-cold 10% sodium hydroxide solution and extracted with ethyl acetate (100 ml). The extract was washed with brine, dried over magnesium sulfate. A solution of p-toluenesulfonic acid (38 g) in acetonitrile (100 ml) was added to this extract to afford a precipitate solid which was collected by filtration, thoroughly washed successively with acetonitrile and n-hexane, and dried in vacuo, 5.2 g of 2,3-diamino-3-(methylthio)acrylonitrile p-toluenesulfonate (Compound No. 21 ) was obtained as light-brown powder: m.p. 181°-183° C. (dec.)

EXAMPLE 6

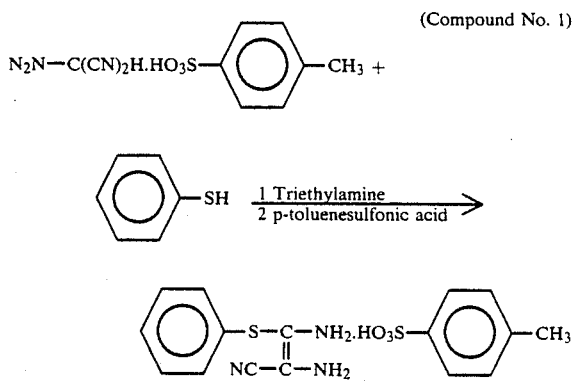

To a stirred suspension of thiophenol (10.5 g), 2-aminoalononitrile p-toluenesulfonate (20 g) in acetonitrile (300 ml) was added triethylamine (20 g) at room temperature. After stirring for 1 hour, the solvent was evaporated under reduced pressure to give the residue to which acetonitrile (200 ml) was added, followed by adding p-toluenesulfonic acid (20 g). A precipitate solid formed was collected by filtration and thoroughly washed successively with acetonitrile and n-hexane to give 7 g of white crystales, Infrared sectrum of this compound was identical with that of 2,3-diamino-3-(phenylthioacrylonitrile)p-toluenesulfonate prepared in example 1.

EXAMPLE 7

(Compound No. 33)

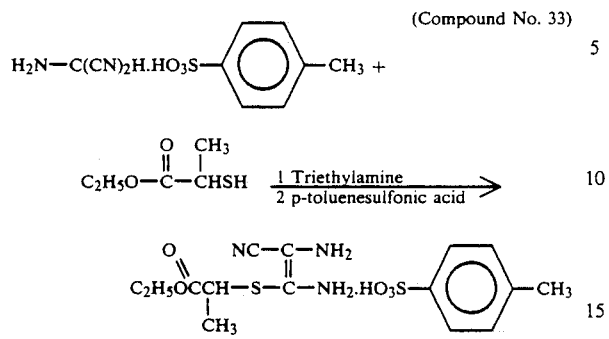

To a suspension of ethyl 2-mercaptoacetate (0.4 g) and 2-aminomalononitrile-p-toluenesulfonate (0.76 g) in acetonitrile (10 ml) added dropwise triethylamine (0.6 g) at room temperature and was stirred for 5 hours. The mixture was evaporated under reduced pressure. Ethyl acetate (20 ml) was added to the residue, washed with water, dried over magnesium sulfate and evaporated again. A solution of p-toluenesulfonic acid (0.6 g) in acetonitrile (20 ml) was added to the residue and allowed to stand overnight in the refregirator. The precipitate solid was collected by filtration, washed thoroughly with acetonitrile and dried in vacuo.

0.46 g of 2,3-diamino-3-(2-ethoxycarbonylethylthio)acrylonitrile p-toluenesulfonate (Compound No. 33) was obtained as white powder: m.p. 197°–199° C. (dec.)

EXAMPLE 8

(Compound No. 1)

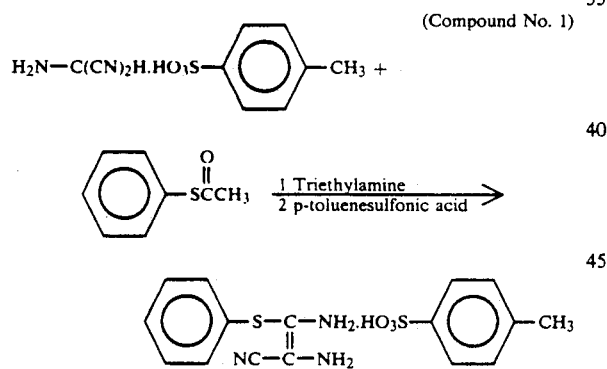

To a suspension of S-phenylthio acetate (0.76 g) and 2-aminomalononitrile p-toluenesulfonate (1.26 g) in acetonitrile (10 ml) was added dropwise triethylamine (1 g) at room temperature and stirring was continued for 30 minutes. After evaporation of the solvent under reduced pressure, a solution of p-toluenesulfonic acid (1 g) in acetonitrile (10 ml) was added to the residue to give a crude compound No. 1 which was purified by thoroughly washing actonitrile and recrystallization from acetonitrile.

EXAMPLE 9

(Compound No. 26)

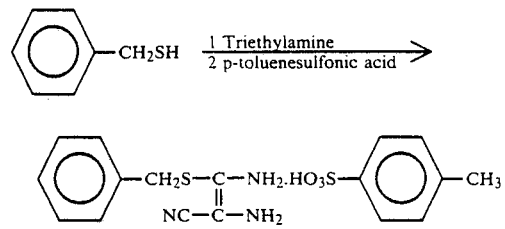

A solution of 2,3-diamino-3-(phenylthio)acrylonitrile (1.9 g), benzyl mercaptan (3.7 g) and triethylamine (3 g) in acetonitrile (30 ml) was heated under reflux overnight. After evaporation of the solvent under reduced pressure, a solution of p-toluenesulfonic acid (1.7 g) in actonitrile (30 ml) was added to the residue. The precipitate solid formed was collected by filtration and thoroughly washed successively with acetonitrile and benzene to give 2.2 g of 2,3-diamino-3-(benzylthio)acrylonitrile p-toluenesulfonate (Compound No. 26) as light brown powder: m.p. 173°–174° C. (dec.)

EXAMPLE 10

(Compound No. 1)

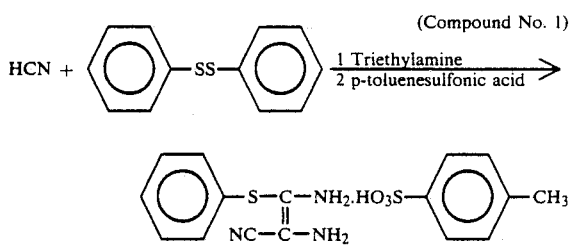

In a 100 ml flask were placed 8.7 g of diphenyl disulfide, 8.1 g of triethylamine and 30 ml of acetonitrile, and 6.5 g of liquid hydrogen cyanide was added to this solution at room temperature and stirred at 40° C. for 1 hour. To the residue left after the evaporation of triethylamine, hydrogen cyanide and a part of acetonitrile, 7.5 g of p-toluenesulfonic acid dissolved in 20 ml acetonitrile was added well stirring to give a pale yellow precipitates which was collected by filtration, and thoroughly washed successively with 20 ml of diethyl ether and 20 ml of n-hexane, dried in a vacuum decicator. 12 g of 2,3-diamino-3-(phenylthio)acrylonitrile p-toluenesulfonate was obtained in a yield of 83% with respect to diphenyl disulfide.

Recrystalization from acetonitrile gave white crystales m.p. 148°–149° C. (dec.)

EXAMPLE 11

(Compound No. 3)

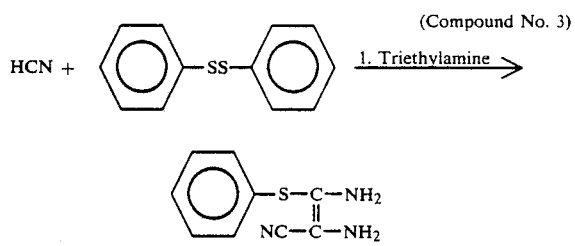

In a 2000 ml flask were placed 218 g of diphenyl disulfide, 202 g of triethylamine and 750 ml of xylene, and 162 g of liquid hydrogen cyanide was added to the solution at 5° C. with stirring. The reaction temperature in the flask rose gradually up to 20° C. after addition was completed and kept at this temperature. After 1 hour, the reaction mixture was poured into 1200 g of 10% sodium hydroxide which is precooled at 5° C. in 3000 ml glass vessel followed by adding 100 ml of n-hexane and stirred for 10 minutes at 5° C. The pale yellow precipitates was filtered, washed with 200 ml of water, 200 ml of brine and 100 ml of n-hexane. The product is dried over vacuum over. 173 g of 2,3-diamino-3-(phenylthio)acrylonitrile in a yield of 90%. Recrystalization from chloroform gave pale yellow needles: m.p. 86.5°-87.5° C. (dec.)

EXAMPLE 12

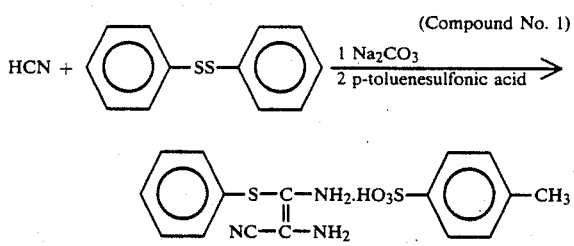

(Compound No. 1)

In a 200 ml flask placed were 8.7 g of diphenyl disulfide, 40 g of 20% sodium carbonate and 30 ml of acetonitrile, and 6.5 g of liquid hydrogen cyanide was added to this solution and stirred at 20° C. for 4 hours. The reaction mixture was extracted with 50 ml of chloroform two times, and chloroform layer was dried over magnesium sulfate. 7.6 g of p-toluenesulfonic acid dissolved in acetonitrile was added to the residue left after the evaporation of chloroform. The resulting pale yellow precipitates were filterd, washed with 20 ml of diethyl ether and 20 ml of n-hexane and dried in a vacuum decicator. 10.9 g of 2,3-diamino-3-(phenylthio)acrylonitrile was obtained in a yield of 75%.

EXAMPLE 13

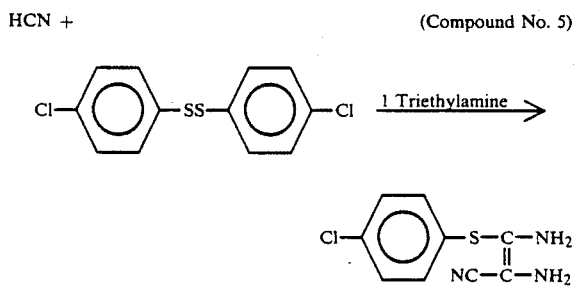

(Compound No. 5)

In a 200 ml flask placed were 11.5 g of di-p-chlorophenyl disulfide, 8.1 g of triethylamine and 30 ml of xylene, and 6.5 g of liquid hydrogen cyanide was added to this solution at 10° C. with stirring. After the addition was completed, the reaction temperature in the flask was kept at 20° C. for 1 hour. Then the reaction mixture which has been cooled to 5° C. was poured into 48 g of 10% sodium hydoxide in 1000 ml glass vessel, and to this resulting reaction mixture 5 ml of n-hexane was added at 5° C. and stirred for 10 minutes. The pale yellow precipitates resulted was filtered, washed successively with 20 ml of water and 20 ml n-hexane and dried in a vacuum decicator. 7.2 g of 2,3-diamino-3-(p-chlorophenylthio)acrylonitrile was obtained in a yield of 80%. Recrystalization from chloroform-n-hexane gave pale yellow powders: m.p. 107°-108° C.

EXAMPLE 14

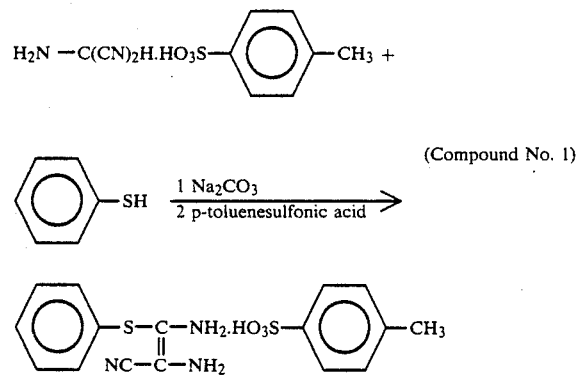

(Compound No. 1)

To a stirred suspension of thiophenol (10.5 g) and 2-aminomalononitrile p-toluenesulfonate (20 g) in acetonitrile (400 ml) was added sodium carbonate (21 g) at room temperature. After stirring for 10 hours, the solid residue was filtered and a half volume of the filtrate was evaporated under reduced. pressure to give the residue to which p-toluenesulfonic acid (20 g) was added. A precipitate solid formed was collected by filtration and thoroughly washed successively with acetonitrile and n-hexane to give 15 g of white crystales. Infrared sectrum of this compound was identical with that of 2,3-diamino-(3-phenylthio)acrylonitrile p-toluenesulfonate prepared in example 1.

Inclusive the above, each compound with the scope of the present invention which can be prepared in analogous method is tabulated in Table 1.

TABLE 1

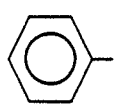

| Compound No. | R | salt | Physical Properties [ ] m.p. °C. |
|---|---|---|---|
| 1 | ⌬- | HO₃S-⌬-CH₃ | [148~149] |
| 2 | " | HCl | [144~145.5] |
| 3 | " | — | [86.5~87.5] |

TABLE 1-continued

Structure
RS—C—NH$_2$
‖
NC—C—NH$_2$

| Compound No. | R | salt | Physical Properties [ ] m.p. °C. |
|---|---|---|---|
| 4 | Cl—C$_6$H$_4$— | HO$_3$S—C$_6$H$_4$—CH$_3$ | [153~154] |
| 5 | " | — | [107~108] |
| 6 | Br—C$_6$H$_4$— | — | [90~93] |
| 7 | $^t$C$_4$H$_9$—C$_6$H$_4$— | — | [69~71.5] |
| 8 | 2-CH$_3$—C$_6$H$_4$— | — | [51~53.5] |
| 9 | O$_2$N—C$_6$H$_4$— | — | [133~114.5] |
| 10 | C$_6$H$_5$—O—C$_6$H$_4$— | — | [104~106] |
| 11 | F—C$_6$H$_4$—O—C$_6$H$_4$— | — | [103~104.5] |
| 12 | C$_6$H$_5$—C$_6$H$_4$— | — | [131~132] |
| 13 | CH$_3$—C$_6$H$_4$—O—C$_6$H$_4$— | — | [119~121.5] |
| 14 | Br—C$_6$H$_4$—C$_6$H$_4$— | — | [120~123] |
| 15 | CH$_3$—C$_6$H$_4$—C$_6$H$_4$— | — | [124~126] |
| 16 | 2-naphthyl | — | [111~112.5] |

TABLE 1-continued

Structure
$$\begin{array}{c} RS-C-NH_2 \\ \parallel \\ NC-C-NH_2 \end{array}$$

| Compound No. | R | salt | Physical Properties [ ] m.p. °C. |
|---|---|---|---|
| 17 | 1-fluoronaphthalen-4-yl | — | [143.5~145.5] |
| 18 | 4-fluorophenyl | — | [78.5~80] |
| 19 | 4-methylphenyl | — | [53~55] |
| 20 | 2,4-dichlorophenyl | — | [144~146] |
| 21 | $CH_3-$ | $HO_3S-C_6H_4-CH_3$ | [181~183] |
| 22 | $C_2H_5-$ | " | [130~131.5] |
| 23 | $C_{10}H_{21}-$ | " | [140~142] |
| 24 | $C_{18}H_{33}-$ | " | [131~132] |
| 25 | $CH_2=CHCH_2-$ | " | [115~117] |
| 26 | $C_6H_5CH_2-$ | " | [173~174] |
| 27 | 4-methylbenzyl | " | [171.5~177.5] |
| 28 | 4-chlorobenzyl | " | [181~183] |
| 29 | $^iC_4H_9-$ | " | [160~162] |
| 30 | cyclohexyl | " | [192~194] |
| 31 | cyclopentyl | " | [187~189] |
| 32 | $ClCH_2CH_2-$ | " | [145~146.5] |

TABLE 1-continued

Structure
$$RS-\underset{\underset{NC-C-NH_2}{\|}}{C-NH_2}$$

| Compound No. | R | salt | Physical Properties [ ] m.p. °C. |
|---|---|---|---|
| 33 | C₂H₅OC(=OCH₃)CH— | " | [197~199] |
| 34 | CH₃OC(=O)CH₂CH₂— | " | [124~126] |
| 35 | HOC(=OCH₃)CH— | " | [210~213] |
| 36 | C₂H₅OC(=O)CH₂SCH₂CH₂— | " | [110~111] |
| 37 | HOCH₂CH₂— | " | [163~165] |
| 38 | HSCH₂CH₂— | " | [130~132] |
| 39 | (furan-2-yl)CH₂— | " | [126~128] |
| 40 | C₂H₅CH(CH₃)— | " | [183~185] |
| 41 | (geranyl-type chain) | " | [183~185] |
| 42 | (farnesyl-type chain) | " | [205~207] |
| 43 | (prenyl-type chain) | " | [165~167] |
| 44 | (thiophen-2-yl)CH₂— | " | [160~162] |
| 45 | (dibenzofuranyl) | — | [70~73] |
| 46 | (cyclohexyl-phenyl) | — | [87~89] |

INDUSTRIAL APPLICABILITY

The diaminoacrylonitrile derivatives of the present invention can be isolated as stable compounds because the introduction of RS-group into 3 position of 2,3-diaminoacrylonitrile contributes to their stability. As the reference example below shows, said derivatives are so highly reactive that it is useful as materials for preparing a wide variety of organic compounds.

Further, as examples above show, said derivatives can be directly synthesized from hydrogen cyanide under mild reaction conditions, hence their manufacture at a low cost is possible. 2-aminomalononitrile is noted as a trimer of hydrogen cyanide but its high cost and lack of stability have put it out of industrial use. In place of this, the invention offers low-cost, stable 2,3-diaminoacrylonitrile derivatives and their manufacturing method, and accordingly its industrial significance is very great.

REFERENCE EXAMPLE 1

White crystals obtained in example 1 was redissolved in a filtrate resulted from the filtration of the crude crystals obtained in example 1. To this solution were added a small amount of triethylamine and then hydrogen cyanide followed by stirring for 10 minutes. Diaminomaleonitrile, a tetramer of hydrogne cyanide, was produced quantitatively.

We claim:

1. A 2,3-diaminoacrylonitrile derivative having the formula $$\begin{array}{c} RS-C-NH_2 \\ \parallel \\ NC-C-NH_2 \end{array}$$

wherein R represents on $C_{1-18}$ alkyl group (which may be substituted by unsubstituted or substituted phenyl groups, halogen atoms, $C_{1-4}$ alkoxycarbonyl groups, $C_{1-2}$ alkoxycarbonyl $C_{1-2}$ alkylthio groups, hydroxy groups, mercapto groups or heterocyclic groups containing oxygen and sulfur atoms); an $C_{3-15}$ alkenyl group; a $C_{5-6}$ cycloalkyl group; a naphthyl group; a benzofuranyl group; or a phenyl group (which may be substituted by halogen atoms, $C_{1-4}$ alkyl groups, cycloalkyl groups, nitro groups, unsubstituted or substituted phenyl or phenoxy groups).

2. A process for the production of a 2,3-diaminoacrylonitrile derivative or salts thereof having the formula $$\begin{array}{c} RS-C-NH_2 \\ \parallel \\ NC-C-NH_2 \end{array}$$

which comprises reacting hydrogen cyanide with a compound having the formula RSSR in the presence of a base at 0°–40° C., wherein the molar ratio of RSSR: base: hydrogen cyanide is at least 1:1:1; wherein R represents an $C_{1-18}$ alkyl group (which may be substituted by unsubstituted or substituted phenyl groups, halogen atoms, $C_{1-4}$ alkoxycarbonyl groups, carboxy groups, $C_{1-2}$ alkoxycarbonyl $C_{1-2}$ alkylthio groups, hydroxy groups, mercapto groups or heterocyclic groups containing oxygen and sulfur atoms); an $C_{3-15}$ alkenyl group; a $C_{5-6}$ cycloalkyl group; a naphthyl group; a benzofuranyl group; or a phenyl group (which may be substituted by halogen atoms, $C_{1-4}$ alkyl groups, cycloalkyl groups, nitro groups, unsubstituted or substituted phenyl or phenoxy groups).

3. A process for the production of a 2,3-diaminoacrylonitrile derivative or salts thereof having the formula $$\begin{array}{c} RS-C-NH_2 \\ \parallel \\ NC-C-NH_2 \end{array}$$

which comprises reacting 2-aminomalononitrile with a compound having the formula RSSR, RSH or RSC—CH$_3$ in the presence of a base wherein R represents an $C_{1-18}$ alkyl group (which may be substituted by unsubstituted or substituted phenyl groups, halogen atoms, $C_{1-4}$ alkoxycarbonyl groups, carboxy groups, $C_{1-2}$ alkoxycarbonyl $C_{1-2}$ alkylthio groups, hydroxy groups, mercapto groups or heterocyclic groups containing oxygen and sulfur atoms); an $C_{3-15}$ alkenyl group; a $C_{5-6}$ cycloalkyl group; a naphthyl group; a benzofuranyl group; or a phenyl group (which may be substituted by halogen atoms, $C_{1-4}$ alkyl groups, cycloalkyl groups, nitro groups, unsubstituted or substituted phenyl or phenoxy groups).

4. The process of claim 2, wherein the molar ratio of RSSR: base: hydrogen cyanide is 1:2:6.

5. The process of claim 2, wherein the reaction is carried out at a temperature range from 5°–20° C.

* * * * *